United States Patent [19]
Stoub et al.

[11] Patent Number: 5,717,213
[45] Date of Patent: Feb. 10, 1998

[54] COLLIMATOR AND SCINTILLATION CAMERA SYSTEM FOR USE IN CARRYING OUT ATTENUATION-CORRECTED SPECT STUDIES OF SMALL BODY ORGANS SUCH AS THE HEART AND BRAIN

[75] Inventors: Everett W. Stoub, Crystal Lake; Reinout F. Vogt, Streamwood, both of Ill.

[73] Assignee: Siemens Medical Systems, Inc., Iselin, N.J.

[21] Appl. No.: 493,875

[22] Filed: Jun. 23, 1995

[51] Int. Cl.⁶ .............................. G01T 1/166; G21K 1/02
[52] U.S. Cl. .................................. 250/363.1; 250/363.04
[58] Field of Search ............................ 250/363.1, 363.04

[56] References Cited

U.S. PATENT DOCUMENTS

| | | | |
|---|---|---|---|
| 5,001,347 | 3/1991 | Hsieh | 250/363.1 |
| 5,576,545 | 11/1996 | Stoub et al. | 250/363.04 |
| 5,608,221 | 3/1997 | Bertelsen et al. | 250/363.03 |

FOREIGN PATENT DOCUMENTS

| | | | |
|---|---|---|---|
| 0 196 538 A1 | 10/1986 | European Pat. Off. | |
| 0 444 324 A2 | 9/1991 | European Pat. Off. | |
| 61-159179 | 7/1986 | Japan | 250/363.1 |
| WO 94/25879 | 11/1994 | WIPO | |

OTHER PUBLICATIONS

Patent Abstracts of Japan, vol. 16, No. 295, 30 Jun. 1992 (C-0957) abstract for JP 4-79939 A (Seiichi) 13 Mar. 1992.

*Primary Examiner*—Constantine Hannaher
*Attorney, Agent, or Firm*—Mark H. Jay

[57] ABSTRACT

In the axial direction, a collimator is a fan-beam collimator. In the transverse direction, the collimator has a set of central magnifying fan beams located between two sets of peripheral magnifying fan beams.

4 Claims, 3 Drawing Sheets

COLLIMATOR AND SCINTILLATION CAMERA SYSTEM FOR USE IN CARRYING OUT ATTENUATION-CORRECTED SPECT STUDIES OF SMALL BODY ORGANS SUCH AS THE HEART AND BRAIN

BACKGROUND OF THE INVENTION

The invention relates to nuclear medicine, and more particularly relates to Single Photon Emission Computed Tomography ("SPECT") nuclear medicine studies. In its most immediate sense, the invention relates to attenuation correction of SPECT studies of small body organs such as the heart and brain.

In a conventional SPECT (Single Photon Emission Computed Tomography) study of an organ such as the heart, a radioisotope (Tc-99m, Tl-201, for example) is administered to the patient and the radioisotope is taken up by the heart muscles. Then, the patient is placed in a scintillation camera system and one or more scintillation camera detectors are rotated about the long axis of the patient. These detectors pick up gamma radiation that leaves the patient, and the resulting data is used to form three-dimensional images ("SPECT images" or "tomographic images") of the distribution of the radioisotope within the patient.

Such three dimensional SPECT images can be calculated based on a set of two-dimensional images ("projections" or "projection images") acquired by the scintillation camera system; this calculation process is known as image reconstruction. The most commonly employed method of image reconstruction is known as "filtered backprojection". When filtered backprojection reconstruction is used to reconstruct SPECT images from scintigraphic projection images obtained from a scintillation camera, some well-known distortions introduce errors ("artifacts") in the result. One of the most important distortions is caused by attenuation of gamma radiation in tissue.

As a consequence of attenuation, image values in the various projections do not represent line integrals of the radioisotope distribution within the body. It is therefore necessary to correct for this, and the process for doing so in SPECT is known as attenuation correction.

Many techniques for attenuation correction in SPECT assume that the linear attenuation coefficient of the body is uniform and impose such uniformity as a mathematical constraint in the image reconstruction process. However, for a very important class of studies, namely cardiac SPECT studies, the linear attenuation coefficient of the body is in fact highly nonuniform. This is because lung tissue has a lower attenuation than do, e.g., the blood and other non-lung tissue.

Thus, in SPECT studies of, e.g., the heart, a SPECT reconstruction of the image of radioactivity within the heart will necessarily contain artifacts caused by the unequal attenuation coefficients of, e.g., the lungs and the body. Such artifacts also appear in SPECT cardiac images taken from obese patients and from large-breasted female patients.

The same problem affects SPECT studies of the human brain; SPECT images of the brain likewise contain attenuation artifacts when the emission data from the brain is not attenuation-corrected. One cause of attenuation artifacts is variations in the bone mass of the patient's skull, particularly in the posterior region of the skull and especially at the visual cortex. Another cause is the size and distribution of the patient's sinuses.

It is known to measure the actual attenuation coefficients of body tissues by placing a line source of gamma radiation on one side of the body and measuring the transmission of the gamma radiation through the body as a function of direction, i.e. collecting transmission CT data, as the line source is scanned across the patient's body. However, the mechanism necessary to scan the line source is complicated and adds expense to the camera system. It would be advantageous to provide apparatus that would acquire the necessary transmission CT data without the need to scan the line source.

Furthermore, when using a focussing collimator to conduct SPECT studies of relatively small organs, such as the heart and the brain, it is usually necessary to limit the magnification used. This is because the organ of interest may be truncated (i.e. may lie partially outside the field of view of the collimator). Such truncation makes it impossible to acquire a full 180° or 360° of data during a SPECT study, and the data deficiency causes "truncation artifacts" i.e. truncation-caused image distortions, to appear in the reconstructed SPECT image.

Accordingly, one object of the invention is to provide apparatus which can be used to magnify the images of small body organs (e.g. the heart and brain) without causing truncation errors, and which does not require the use of a scanning line source when measuring transmission CT data preliminary to carrying out attenuation correction.

Another object of the invention is, in general, to improve on apparatus of this general type.

In accordance with the invention, a collimator is provided and used on a scintillation camera of the type which is used to carry out SPECT studies. In the axial direction, the collimator is a fan beam collimator focussing to a line source axis which is perpendicular to the axis of rotation. Therefore, a line source located along the line source axis will irradiate all points on the detector. For this reason, the line source need not be scanned to accumulate all necessary transmission CT data.

In the transverse direction, the collimator focusses to a set of central magnifying fan beams located between two sets of peripheral minifying fan beams. Each fan beam in the set of central magnifying fan beams has a focus that is located between the line source axis and the axis of rotation along a focal line. Each fan beam in the sets of peripheral minifying fan beams has a focal point which is more distant from the axis of rotation than is the collimator from the axis of rotation.

This transverse focussing scheme accomplishes two seemingly contradictory objectives. First, the image of a small body organ located within a central region of the collimator will be magnified. Second, even if the small body organ extends slightly outside this central region, truncation artifacts will not come about, his is because the image of the otherwise-truncated portion of the body organ will be made incident on the detector in minified form.

In accordance with a first preferred embodiment of the invention, the above-referenced focal line symmetrically intersects the extreme planes of focus as viewed in the axial direction, i.e. the extreme planes of focus and the focal line form an isosceles triangle. This preferred embodiment is particularly well-suited for cardiac applications.

In accordance with a second preferred embodiment of the invention, the above-referenced focal line asymmetrically intersects the extreme planes of focus as viewed in the axial direction, i.e. the extreme planes of focus and the focal line form a scalene triangle. This preferred embodiment is particularly well-suited for imaging the human brain, because in brain studies the detector has a caudal tilt to decrease the distance between the detector and the patient's head.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
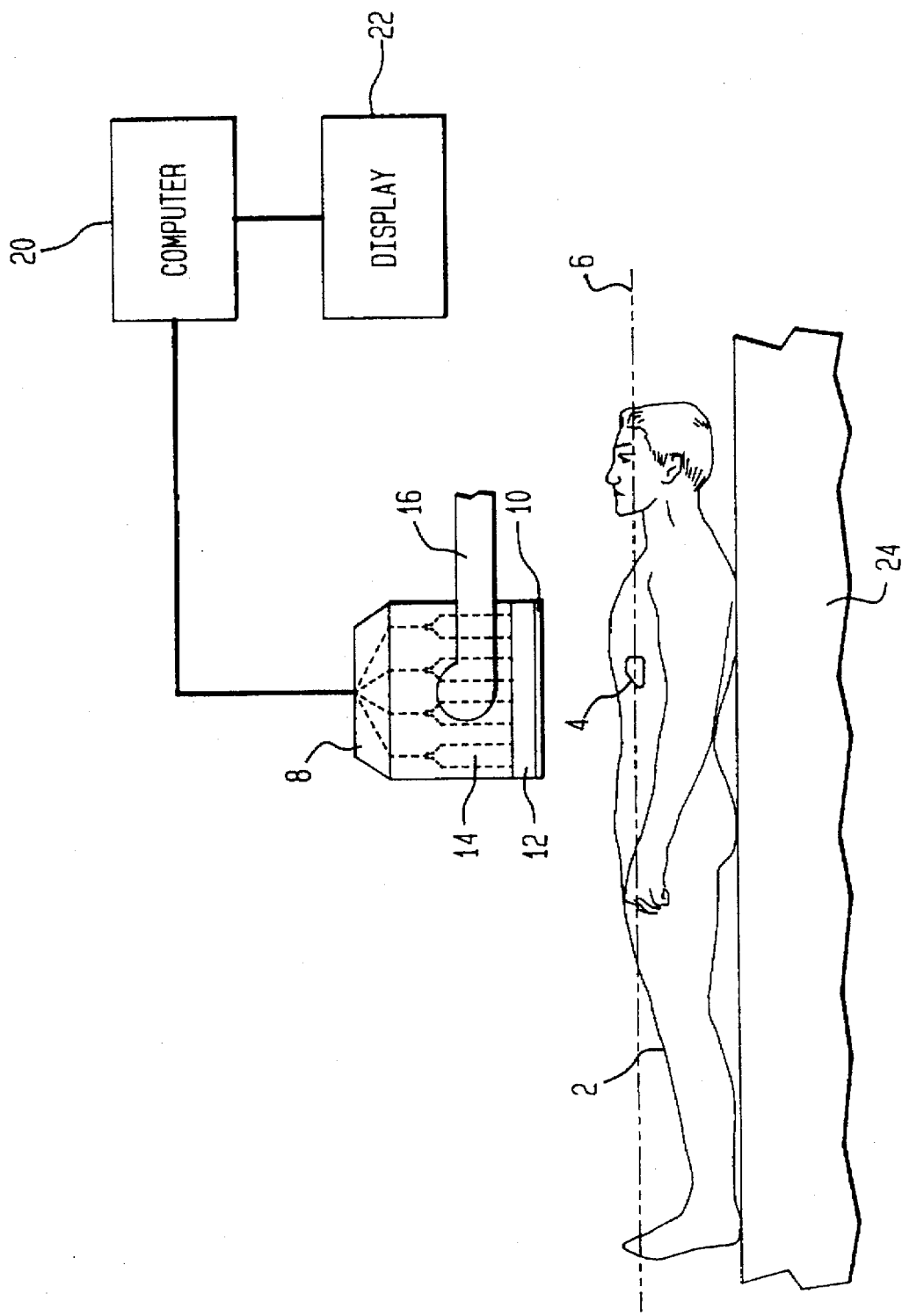
FIG. 1 is a block diagram which schematically illustrates a scintillation camera system in accordance with the invention.

In a cardiac SPECT study such as is illustrated in FIG. 1, a radioisotope (e.g. Tl-201) is administered to a patient 2. The radioisotope is taken up in the patient's heart 4. The detector 8 of a scintillation camera system is rotated about an axis of rotation 6; as shown, the patient 2 is positioned so the axis of rotation 6 passes through the heart 4.

The detector 8 is rotated about the axis of rotation 6 by the yoke 16 of a camera gantry. Gamma radiation from the heart 4 is collimated by a collimator 10 which is described in more detail below. The collimated gamma radiation is made incident upon a scintillation crystal 12, where it interacts with the crystal 12 to form flashes of scintillation light ("scintillation events"). These scintillation events—representing emission data from the patient—are detected by an array of photomultiplier tubes 14; each photomultiplier tube produces an electrical signal. These signals are combined and processed by appropriate circuitry (not shown) and the resulting electrical signals are routed to a computer 20. The computer 20 produces, by suitable programming, a three-dimensional image of the heart 4; the image can be displayed on a display 22.

To accumulate transmission CT data about the patient 2, a line source 24 is provided. The line source 24 is filled with another radioisotope (e.g. Gd-153), and the Gd-153 scintillation events at the detector 8 represent transmission CT data from which the attenuation coefficients of various portions of the patient 2 can be determined.

It will be understood that in e.g. a brain study, the patient 2 would be relocated so that the axis of rotation 6 passed through the brain (not shown) of the patient 2.

Figure 2:
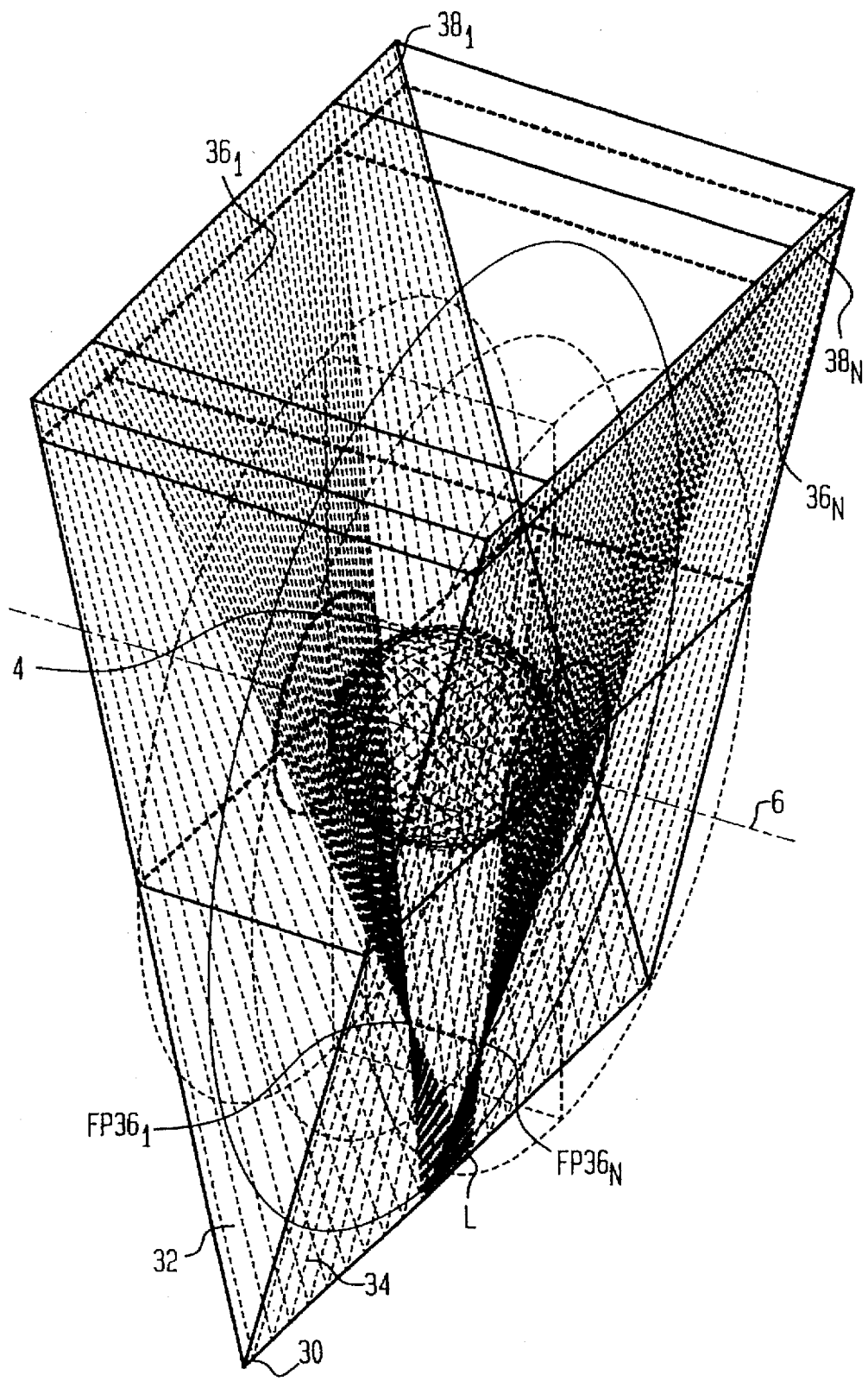
FIG. 2 schematically illustrates the focussing scheme of a first preferred embodiment of a collimator in accordance with the invention.

FIG. 2 schematically illustrates the focussing scheme of a first preferred embodiment of a collimator in accordance with the invention. As is understood by persons skilled in the art, a scintillation camera collimator is made of a material (e.g. lead) opaque to gamma radiation. The collimator has a large number (e.g. 150,000) of relatively thin channels; only gamma rays which are parallel to these channels are transmitted through the collimator to become incident upon the scintillation crystal 12. For purposes of this description, the actual structure of the preferred embodiment has not been illustrated because that would be confusing, but as presently contemplated, the preferred embodiments of collimators in accordance with the invention are cast collimators having rectangular shapes.

In the axial direction, the first preferred embodiment is a fan-beam collimator which focuses to a line source axis 30. The line source axis 30 is at right angles to the axis of rotation 6. In FIG. 2, two extreme planes of focus 32 and 34 are shown; these bound the limits of focus of the axially-directed fan-beam focussing scheme. However, there are many other planes of focus between the extreme planes of focus 32 and 34; the number of such planes is determined by trading off the desired resolution of the collimator against the desired sensitivity of the collimator and is not a part of the invention.

In the transverse direction, the first preferred embodiment has a set of central magnifying fan beams. The first of these central magnifying fan beams is shown as $36_1$ and the last of these central magnifying fan beams is shown as $36_N$; the central magnifying fan beam $36_1$ is coextensive with the extreme plane of focus 32 and the central magnifying fan beam $36_N$ is coextensive with the extreme plane of focus 34. The intermediate central magnifying fan beams located between the central magnifying fan beams $36_1$ and $36_N$ are not shown; the number of such intermediate central magnifying fan beams is determined by trading off the desired resolution of the collimator against the desired sensitivity of the collimator and is not a part of the invention.

The set of central magnifying fan beams is located between two sets of peripheral minifying fan beams. The sets of peripheral minifying fan beams are mirror images of each other, so both are accurately described when one is described. Each set of peripheral minifying fan beams has N elements; as above, N is determined by trading off the desired resolution of the collimator against the desired sensitivity of the collimator and is not a part of the invention. The first peripheral minifying fan beam $38_1$ in the first set of peripheral minifying fan beams $38_1 \ldots 38_N$ is coextensive with the extreme plane of focus 32 and the last peripheral minifying fan beam $38_N$ in the first set of peripheral minifying fan beams $38_1 \ldots 38_N$ is coextensive with the extreme plane of focus 34.

Each of the peripheral minifying fan beams has a focal point located above the collimator, i.e. located further away from the axis of rotation 6 than is the detector 8. Each of the intermediate central magnifying fan beams has a focal point; the focal point for the central magnifying fan beam $36_1$ is $FP36_1$, the focal point for the central magnifying fan beam $36_N$ is $FP36_N$, and so on.

In the first preferred embodiment of the invention, which is designed for use in SPECT studies of the heart 4, the focal points $FP36_1 \ldots FP36_N$ all lie along a focal line L, and the focal line L intersects the extreme planes of focus 32 and 34 symmetrically. As a result, when viewed axially, the focal line L and the extreme planes of focus 32 and 34 produce an isosceles triangle.

Figure 3:
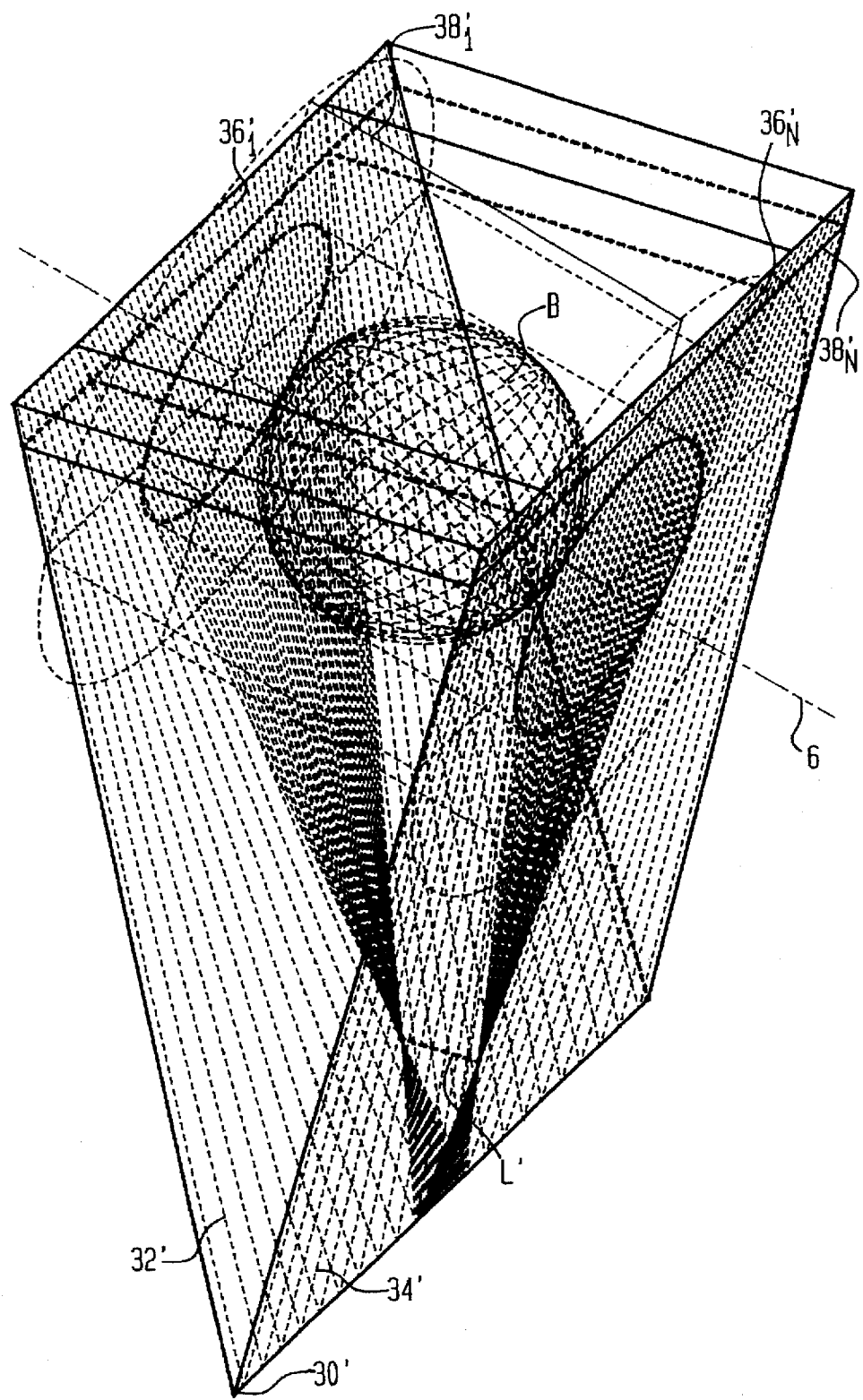
FIG. 3 schematically illustrates the focussing scheme of a second preferred embodiment of a collimator in accordance with the invention.

In the second preferred embodiment of the invention as illustrated in FIG. 3, elements corresponding to elements in FIG. 2 have the same reference number but are primed. All the geometrical relations described in connection with FIG. 2 remain true, except that the focal line L' intersects the extreme planes of focus 32' and 34' asymmetrically. As a result, when viewed axially, the focal line L' and the extreme planes of focus 32' and 34' produce a scalene triangle. This is because when imaging the brain B, the detector 8 is conventionally angulated with a "caudal tilt" to minimize the overall distance between the detector and the patient's head (see, e.g., angle φ in U.S. Pat. No. 5,001,347).

Although a preferred embodiment has been described above, the scope of the invention is limited only by the following claims:

I claim:

1. A collimator for use in a SPECT study during which a collimated detector is rotated about an axis of rotation, a line source oriented along a line source axis at right angles to the axis of rotation is opposed to the detector, and emission data and transmission CT data are acquired simultaneously, the collimator being made of material opaque to gamma radiation and focussing as follows:

in an axial direction, as a fan beam projecting toward the axis of rotation from the line source axis and between two extreme planes of focus; and in a transverse direction, as a set of central magnifying fan beams located between two sets of peripheral minifying fan beams, all of said central and peripheral fan beams extending between the axis of rotation and the collimator, each fan beam in said set of central magnifying fan beams having a focus located between the line source axis and the axis of rotation along a focal line, and each fan beam in said sets of peripheral minifying fan beams having a focal point which is more distant from the axis of rotation than is the detector from the axis of rotation.

2. The collimator of claim 1, wherein the two extreme planes of focus viewed parallel to their surfaces and the focal line define an isosceles triangle.

3. The collimator of claim 1, wherein the two extreme planes of focus viewed parallel to thier surfaces and the focal line define a scalene triangle.

4. A scintillation camera system for use in SPECT studies during which a collimated detector is rotated about an axis of rotation, a line source oriented along a line source axis at right angles to the axis of rotation is opposed to the detector, and emission data and transmission CT data are acquired simultaneously, comprising:

a detector for detecting gamma radiation and producing electrical output signals;

means for reconstructing images from said electrical output signals;

a gantry for rotating the detector about the axis of rotation;

a line source opposed to the detector and oriented along a line source axis at right angles to the axis of rotation; and a collimator attached to the detector, the collimator being made of material opaque to gamma radiation and focussing in an axial direction, as a fan beam projecting toward the axis of rotation from the line source axis and between two extreme planes of focus; and in a transverse direction, as a set of central magnifying fan beams located between two sets of peripheral minifying fan beams, all of said central and peripheral fan beams extending between the axis of rotation and the collimator, each fan beam in said set of central magnifying fan beams having a focus located between the line source axis and the axis of rotation along a focal line, and each fan beam in said sets of peripheral minifying fan beams having a focal point which is more distant from the axis of rotation than is the collimator from the axis of rotation.

* * * * *